US009862940B2

(12) United States Patent
Glaubitt

(10) Patent No.: US 9,862,940 B2
(45) Date of Patent: *Jan. 9, 2018

(54) SILICA SOL MATERIAL FOR PRODUCING BILOGICALLY DEGRADABLE AND/OR RESORBABLE SILICA GEL MATERIALS, THE PRODUCTION AND USE THEREOF

(75) Inventor: Walther Glaubitt, Wuerzburg (DE)

(73) Assignee: BAYER INTELLECTUAL PROPERTY GMBH, Monheim am Rhein (DE)

( * ) Notice: Subject to any disclaimer, the term of this patent is extended or adjusted under 35 U.S.C. 154(b) by 340 days.

This patent is subject to a terminal disclaimer.

(21) Appl. No.: 12/523,102

(22) PCT Filed: Jan. 10, 2008

(86) PCT No.: PCT/EP2008/000124
§ 371 (c)(1),
(2), (4) Date: Feb. 24, 2010

(87) PCT Pub. No.: WO2008/086970
PCT Pub. Date: Jul. 24, 2008

(65) Prior Publication Data
US 2011/0183419 A1 Jul. 28, 2011

(30) Foreign Application Priority Data

Jan. 15, 2007 (DE) .................. 10 2007 002 896
Dec. 19, 2007 (DE) .................. 10 2007 061 873

(51) Int. Cl.
C12N 5/00 (2006.01)
C07F 7/02 (2006.01)
(Continued)

(52) U.S. Cl.
CPC .......... *C12N 11/14* (2013.01); *C04B 35/6224* (2013.01); *C08G 77/02* (2013.01);
(Continued)

(58) Field of Classification Search
CPC .... C04B 35/6224; C08G 77/02; C08G 77/18; D01F 9/08; Y10T 442/3976; Y10T 442/696
(Continued)

(56) References Cited

U.S. PATENT DOCUMENTS 5,618,628 A 4/1997 Volpe
5,939,094 A 8/1999 Durif et al.
(Continued)

FOREIGN PATENT DOCUMENTS

DE 19609551 9/1997
DE 199 59 750 C1 5/2001
(Continued)

OTHER PUBLICATIONS

Machine translation of Glaubitt (DE19609551).*
(Continued)

Primary Examiner — Jun Li
(74) Attorney, Agent, or Firm — McBee Moore Woodward & Vanik IP, LLC

(57) ABSTRACT

The invention concerns a novel silica sol material and its use for producing bioabsorbable and biodegradable silica gel materials having improved properties. The materials such as for example fibers, fibrous nonwoven webs, powders, monoliths and/or coatings are used, for example, in medical technology and/or human medicine, in particular for wound treatment.

13 Claims, 3 Drawing Sheets

(51) Int. Cl.
*D01D 5/00* (2006.01)
*D03D 15/00* (2006.01)
*D04H 13/00* (2006.01)
*C12N 11/14* (2006.01)
*C04B 35/622* (2006.01)
*C08G 77/02* (2006.01)
*C08L 83/02* (2006.01)
*D01F 9/08* (2006.01)

(52) U.S. Cl.
CPC .......... *C08L 83/02* (2013.01); *C12N 5/0068* (2013.01); *D01F 9/08* (2013.01); *C12N 2533/10* (2013.01); *Y10T 442/3976* (2015.04); *Y10T 442/696* (2015.04)

(58) Field of Classification Search
USPC .......................................... 423/335; 435/398
See application file for complete search history.

(56) References Cited

U.S. PATENT DOCUMENTS

| | | | |
|---|---|---|---|
| 2004/0033187 A1 | 2/2004 | Peltola et al. | |
| 2004/0197414 A1* | 10/2004 | Ahola et al. | 424/489 |
| 2006/0161089 A1 | 7/2006 | Thierauf et al. | |

FOREIGN PATENT DOCUMENTS

| | | |
|---|---|---|
| DE | 102004063599 | 7/2006 |
| DE | 60035672 T2 | 4/2008 |
| EP | 0 297 176 A1 | 4/1989 |
| EP | 1262542 | 12/2002 |
| RU | 2208582 C2 | 7/2003 |
| RU | 2272617 C2 | 3/2006 |
| WO | 00/50349 | 8/2000 |
| WO | 2006/069567 | 7/2006 |

OTHER PUBLICATIONS

English translation of DE19609551C, publication date Jul. 1997.*
Biological Evaluation of Medical Devices, Part 5: Tests for in vitro cytotoxicity. DIN EN ISO 10993-5, 1999.
International Search Report from PCT/EP2008/000124; dated May 8, 2008 (5 pages).
Sefcik et al. "Kinetic and Thermodynamic Issues in the Early Stages of Sol-Gel Processing Using Silicon Alkoxides", Catalysis Today 35 (1997) 205-223.
Kursawe, Monika et al., "Biodegradable Silica Fibers from Sols", Journal of Sol-Gel Science and Technology, Jan. 1998, pp. 267-271, vol. 13.

* cited by examiner

SILICA SOL MATERIAL FOR PRODUCING BILOGICALLY DEGRADABLE AND/OR RESORBABLE SILICA GEL MATERIALS, THE PRODUCTION AND USE THEREOF

CROSS REFERENCE TO RELATED APPLICATIONS

This application is a §371 National Stage Application of PCT/EP2008/000124 filed Jan. 15, 2007 which claims priority from German Applications 10 2007 002 896.4 filed Jan. 15, 2007 and 10 2007 061 873.7 filed Dec. 19, 2007.

BACKGROUND OF THE INVENTION

Field of the Invention

The invention concerns a novel silica sol material for producing biodegradable and/or absorbable silica gel materials having improved properties and also a process for its production and its use. The invention also concerns biodegradable and/or bioabsorbable silica gel fibre materials.

Description of Related Art

Diverse efforts are underway to develop biodegradable and/or bioabsorbable materials for various applications in human medicine and medical technology. These sectors moreover have higher and higher requirements, particularly with regard to the biocompatibility, biological activity and the toxicological properties of the materials.

Absorbable silica gels are known in the prior art. DE 196 09 551 C1 describes biodegradable, bioabsorbable fibrous structures. These fibres are obtainable in a sol-gel process by drawing threads from a spinning dope and drying them where appropriate. The spinning dope comprises one or more partially or completely hydrolytically condensed compounds of silicon which are derived by hydrolytic condensation from monomers of the general formula $SiX_4$. These fibres have the disadvantage that, in a degradation directly after the spinning operation, they do not produce good results in cytotoxicity tests and in some instances have to be rated as cytotoxic. Such toxicity is generally unwelcome for use in human medicine or medical technology, for example in the sector of wound healing. The process for producing the fibres according to DE 196 09 551 C1, moreover, has the disadvantage that the resulting mixture after the removal of the solvent in the hydrolysis condensation step is already a multiphase mixture and has to be subjected to a filtration to remove the solids formed. In addition, the formation of the solid phase and the mandatory filtration step mean that a large proportion of the spinnable sol is lost. Nor does the process of DE 196 09 551 C1 safely suppress the formation of a not inconsiderable proportion of a solid phase, in particular a gel formation, during ripening. This further reduces the proportion of spinnable sol dope.

Irrespective of this, it has been possible to show that the inventive fibres and fibrous nonwoven webs have improved wound healing properties. Furthermore, the inventive fibres and fibrous nonwoven webs are particularly suitable for use as cell support structures.

SUMMARY OF THE INVENTION

The present invention has for its object to provide a novel silica sol material for producing biodegradable and/or bioabsorbable silica gel materials. The present invention further has for its object to provide biodegradable and/or bioabsorbable silica gel materials having improved cytotoxicity and/or wound healing properties. A further object can be considered that of providing improved cell support structures, for example for in vitro production of skin implants, cartilage and bone.

This object is achieved by a silica sol material according to Claim 1. According to Claim 1, a silica sol material is obtainable by a) conducting a hydrolysis condensation reaction of one or more silicon compounds of the formula I

where the X radicals are the same or different and denote hydroxyl, hydrogen, halogen, amino, alkoxy, acyloxy, alkylcarbonyl and/or alkoxycarbonyl and are derived from alkyl radicals which constitute optionally substituted straight-chain, branched or cyclic radicals having 1 to 20 carbon atoms, preferably having 1 to 10 carbon atoms, and may be interrupted by oxygen or sulphur atoms or by amino groups, under acidic catalysis at an initial pH of 0 to ≤7 in the presence or absence of a water-soluble solvent at a temperature of 0° C. to 80° C. for at least 16 h, b) then evaporating to form a single-phase solution having a viscosity ranging from 0.5 to 2 Pa·s at a shear rate of 10 $s^{-1}$ at 4° C., c) then cooling this solution, and d) subjecting the cold solution to a kinetically controlled ripening to form a homogeneous single-phase sol.

In step a) an X radical of one or more different silicon compounds of the formula (I) is used:

in which the X radicals are the same or different and are each hydroxyl, hydrogen, halogen, amino, alkoxy, acyloxy, alkylcarbonyl and/or alkoxycarbonyl and are derived from alkyl radicals which constitute optionally substituted straight-chain, branched or cyclic radicals having 1 to 20 carbon atoms, preferably having 1 to 10 carbon atoms, and may be interrupted by oxygen or sulphur atoms or by amino groups.

DETAILED DESCRIPTION OF A PREFERRED EMBODIMENT

Figure 1A:
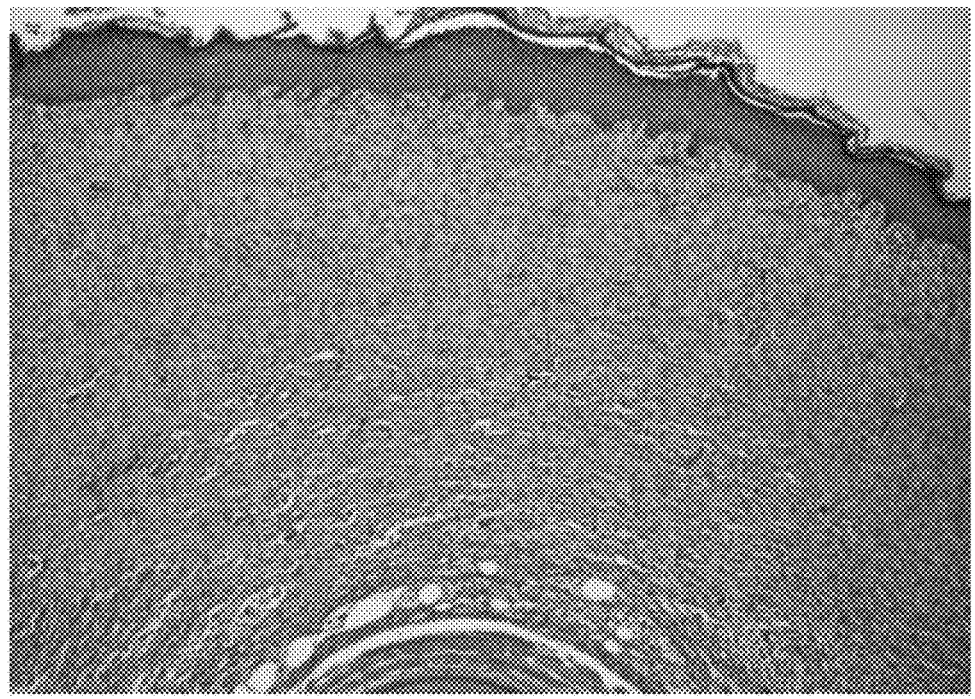
FIG. 1a depicts results of histological tests of KG211 animals 28 days after the generation of wounds.

In a preferred embodiment of the invention, X in the formula (I) is an optionally substituted straight-chain, branched and/or cyclic alkoxy radical having 1 to 20 carbon atoms, preferably having 1 to 10 carbon atoms. More preferably, X in the formula (I) is an optionally substituted straight-chain and/or branched $C_1$-$C_5$ alkoxy radical. Particular preference is further given to substituted, but preferably unsubstituted, straight-chain and/or branched $C_2$-$C_3$ alkoxy radicals, for example ethoxy, N-propoxy and/or isopropoxy.

In accordance with the present invention, it is very particularly preferable to use tetraethoxysilane (TEOS) as silicon compound in the hydrolysis condensation reaction of the present invention. Ethanol or a water/ethanol mixture may preferably be used as water-soluble solvent. The silicon compound/ethanol ratio can be ≥1.

The initial pH of 0 to ≤7, preferably of 2 to 5, is established in a preferred embodiment of the invention with nitric acid acidified water. Other acidic mixtures and/or solutions which can form NO or NO2 in a localized manner are, however, also suitable for the performance of the present invention. These may, for example, be acidic mixtures and/or solutions which, in a physiological environment, with molecular oxygen, by an enzymatic method (by means of a nitroxide synthase, NOS), form nitrogen monoxide (NO) which is in turn converted rapidly to NO2 by the body, or they may also be organic nitrates or nitrate esters (so-called NO donors), e.g. ethyl nitrate, which form NO with the aid of an organic nitrate reductase. For this enzymatic release of NO, thiol groups (cysteine) are required.

In addition to dilute nitric acid, therefore, in accordance with the present invention, an aqueous or alcoholic solution (more preferably: an aqueous dilute ethanolic solution) of a physiologically compatible acid (e.g. citric acid, succinic acid, tartaric acid, acetic acid or ascorbic acid) and at least one essential amino acid (e.g. L-arginine, more preferably: L-valine, L-leucine, L-isoleucine, L-phenylalanine, L-thyroxine, L-methionine, L-lysine or L-tryptophan) or non-essential amino acid (e.g. L-glutamine, L-glutamic acid, L-asparagine, L-aspartic acid, L-cysteine, L-glycine, L-alanine, L-proline, L-histidine, L-tyrosine) is also suitable as a substrate of the NOS for adjusting the pH to the desired value in the weakly to moderately strongly acidic range.

In a preferred embodiment, the hydrolysis condensation reaction is conducted with a silicon compound and nitric acid acidified water in a molar ratio between 1:1.7 and 1:1.9, more preferably in a ratio between 1:1.7 and 1:1.8. The nitric acid acidified water may be used in the form of 0.01 N $HNO_3$.

The hydrolysis condensation is conducted over a period of at least 16 h, preferably of at least 18 h, at a temperature of 0° C. to 80° C., preferably of 0° C. to 78° C., more preferably at 20-60° C., even more preferably at about 20° C. to about 50° C. and, for example—when the inventive materials are used for wound treatment—at room temperature (about 20 to about 25° C.) or at about 37° C.

In a preferred embodiment of the present invention, the hydrolysis can be conducted at room temperature over a period ranging from at least 16 hours, preferably at least 18 hours to 4 weeks. The hydrolysis time preferably ranges from 24 h to 18 days and more preferably from 3 to 8 days. It was determined that, surprisingly, an extended hydrolysis condensation time compared with the hitherto customary times of a few hours at room temperature makes it possible to obtain, after removal of the solvent in step b), a homogeneous single-phase solution which is no longer in need of filtration prior to ripening in step d).

The first hydrolysis condensation reaction is preferably conducted batchwise in a stirred vessel or a single-neck round-bottom flask with a stirrer bar. The silicon compound of the formula (I) (e.g. TEOS) and the solvent (e.g. ethanol) are preferably initially charged. Subsequently, the acid is added rapidly, preferably in the form of 0.01 N $HNO_3$ (e.g. 0.01 mol of $HNO_3$ per mole of TEOS). Owing to the acid strength in the reaction mixture, the first hydrolysis condensation reaction proceeds rapidly, and the contents of the vessel are heated by about 40° C. before the temperature begins to fall during the reaction time (i.e. in step a)) (as a consequence of natural cooling to ambient temperature or heating medium temperature).

The removal of the water-soluble solvent (e.g. ethanol, water) in step (b) is, in a preferred embodiment of the invention, conducted in a closed apparatus in which mixing is possible (preferably rotary evaporator and/or stirred tank) with simultaneous removal of the solvent (water, ethanol) by evaporation at a pressure of 1 to 1013 mbar, preferably at a pressure of <600 mbar, optionally with continuous supply of a chemically inert entraining gas to lower the partial pressure of the evaporating components of 1-8 m3/h (preferably 2.5 to 4.5 m3/h), a reaction temperature of 30° C. to 90° C., preferably 60-75° C., more preferably 60-70° C., and preferably with gentle mixing of the reaction system up to 80 rpm (preferably at 20 rpm to 60 rpm) down to a viscosity of the mixture of 0.5 to 30 Pa·s at a shear rate of 10 s−1 at 4° C., preferably 0.5 to 2 Pa·s at a shear rate of 10 s−1 at 4° C., more preferably approx. 1 Pa·s (measurement at 4° C., shear rate 10 s−1).

In accordance with the present invention, "entrainment gas stream" refers to a gas stream which is supplied to the gas volume via the liquid phase of the reaction system. To maintain the isobaric conditions in the reaction vessel, this must remove a gaseous volume flow which consists both of the "entrainment gas" and of the component(s) to be evaporated. The resulting lowering of the partial pressure, i.e. the reduction in the content of the component or of the component mixture to be evaporated in the gas space, increases the driving force for the evaporation of the solvent at the liquid surface.

In a particularly preferred embodiment, the "entrainment gas stream" is distributed by means of a gas distributor arranged suitably in the gas space of the apparatus such that sufficient entrainment gas exchange is ensured just above the liquid surface but without flow toward the liquid surface in a direct convective manner. In an extreme case, the latter can lead to localized gelation, which is undesired. Gas distributors by means of which this embodiment can be implemented are known to those skilled in the art.

As a result of the advancing reaction/polymerization (recognizable by a rise in viscosity), the phase equilibrium shifts, such that the corresponding equilibrium pressure of the solvent in the vapour phase becomes ever lower. When the equilibrium pressure falls to the total pressure in the gas phase, the evaporation ceases.

In order to evaporate further solvent, the pressure must therefore optimally be lowered, the entrainment gas stream adapted variably and/or the temperature increased.

In a preferred embodiment of the present invention, at least one of the process parameters of pressure, entrainment gas stream and/or temperature must be adjusted variably in time.

In a preferred embodiment of the invention, the evaporation in step b) is effected at a constant temperature and pressure variable with time.

In a preferred embodiment of the invention, the chemically inert entrainment gas stream used to lower the partial pressure is nitrogen and/or air.

In a preferred embodiment of the invention, the water-soluble solvent is removed by means of a combination of vacuum and entrainment gas stream. In this embodiment of the invention, the total pressure and entrainment gas stream can be adjusted independently of one another in a constant manner or variably with time. In this embodiment of the invention, ideally, at least one of the process parameters of pressure, entrainment gas stream and/or temperature is adjusted variably with time. This makes it possible, for example, in an integral manner, to achieve a particular reaction time at a desired degree of evaporation and/or to adjust the evaporation rate to the reaction kinetics.

In a preferred embodiment of the invention, the evaporation in step b) will be effected at a constant temperature and a pressure variable with time, the pressure being lowered up to the end of the second hydrolysis condensation reaction, proceeding from standard pressure or slightly reduced pressure, to <600 mbar, preferably <500 mbar, more preferably <100 mbar.

In the combination method (vacuum with entrainment gas stream), a constant or variable reduced pressure of <600 mbar is preferred.

Temperatures above 60° C. are particularly preferred in order to favour a reductive conversion of the HNO3 to NO at the concentration of $HNO_3$ which otherwise rises significantly in the residual solvent. This very volatile gas (standard boiling point about −150° C.), after escaping from the liquid phase on contact with air, is oxidized to the low-boiling NO2 (BP about 21° C.), which is removed from the system with the waste air or gas stream. In this way, the acid concentration in the inventive material is restricted or reduced. Alternatively, the acid strength can, however, also be reduced in one of the subsequent steps, for example by venting the solid body, for example as a fibrous nonwoven web.

When, however, the organic acid/arginine system is used instead of nitric acid, the pH is increased or the acid strength is reduced, if desired, for example, by means of Tris solutions (when the acid, for example acetic acid, cannot be driven out) just before the application by rinsing in an aqueous Tris solution.

Surprisingly, in comparison to DE 196 09 551 C1, it has been discovered that gentle mixing of the reaction system at 20 rpm to 80 rpm allows the formation of a concentration gradient over the height of the mixture in the reaction vessel during the reactive evaporation (step b) to be prevented. Together with the prolonged hydrolysis condensation reaction time of at least 16 hours, this contributes to at least 70%, preferably at least 80% and most preferably at least 90% of the overall reaction mixture being extrudable in the process according to the invention.

Step (b) is preferably performed until a single-phase solution with a viscosity in the range of 0.5 to 2 Pa·s is formed at a shear rate of 10 s−1 at 4° C., preferably approx. 1 Pa·s (measurement at 4° C., shear rate 10 s−1).

In a preferred embodiment of the invention, the progress of the reaction is monitored in step b) via the viscosity.

The homogeneous and single-phase solution resulting from the hydrolysis condensation reaction in step b) can subsequently be cooled and advantageously subjected quantitatively, and optionally without filtration, to a kinetically controlled ripening.

The ripening (step c)) in the present invention can be carried out at a temperature of −20° C. to 10° C. and preferably at 2° C. to 4° C. (for example in a refrigerator). It is particularly preferable to perform the ripening at 4° C. The low temperature means that a further condensation can take place under kinetically controlled conditions during the ripening time, proceeding from the silicon compounds described above in formula (I). Oligomeric and/or polymeric siloxanes and/or silanols can be formed in this mixture. The oligomers and/or polymers can also aggregate via hydrogen bonds. In accordance with the present invention, a pseudoplastic homogeneous single-phase sol dope is attainable after the ripening. Advantageously, in accordance with the present invention, the competing formation of a three-dimensional polymeric gel network can therefore be very substantially suppressed. It is therefore possible to recover a homogeneous sol dope which has no solid second phase, in particular very substantially no gel phase.

The ripening time in step d) in the present invention can be in the range from 3 days to 4 weeks, preferably at least 10 days, more preferably between 14-40 days, for example between 14 and 28 days, more preferably at least 25 days and—especially when the inventive materials are used for wound treatment—between 25 and 40 days. Preferably in accordance with the present invention, the sol obtained in step d) has a viscosity between 30 and 100 Pa·s (shear rate 10 s−1 at 4° C.) with a loss factor (at 4° C., 10 l/s, 1% deformation) of 2 to 5, preferably of 2.5 to 3.5 (the loss factor is the quotient of the viscous to elastic proportion of the dynamic viscosity). These conditions for the ripening are especially preferred when the silica sol is to be extruded to a fibre after step d).

If the inventive fibres/fibrous nonwoven webs are to be used for wound treatment, the sol obtained in step d) preferably has a viscosity of 35 to 75 Pa·s (shear rate 10 s−1 at 4° C.) and more preferably of 35 to 45 Pa·s (shear rate 10 s−1 at 4° C.), preferably at a loss factor (at 4° C., 10 l/s, 1% deformation) of 2.5 to 3.5.

Too high a loss factor means too high an elasticity of the material, which counters, for example, the formation of a stable thread in the course of extrusion (gelation, tearing of the thread). At too low a loss factor, the material is so free-flowing that stable thread formation is not possible (dripping).

The conditions in the ripening time may vary when the inventive silica sol is subsequently to be processed to a powder instead of to an extrudable fibre. The dynamic viscosity at the end of step (d) in this case is preferably about 60 Pa·s (shear rate 10 s−1 at 4° C.).

In the case of processing of the silica sol to a monolith, the dynamic viscosity at the end of (d) is preferably greater than or equal to 70 Pa·s (shear rate 10 s−1 at 4° C. When the silica sol is to be used to coat bodies or surfaces, the dynamic viscosity, according to the desired layer thickness, is less than or equal to 10 Pa·s (shear rate 10 s−1 at 4° C.).

Preferably, the sol dope obtained can be used at least approximately quantitatively in further production steps and/or operations for biodegradable and/or absorbable silica gel materials. Preferably, the sol obtained in step d) is spinnable. In a further step d), a spinning operation can be envisaged in accordance with the present invention.

Such a spinning process step can be carried out under customary conditions, for example as described in DE 196 09 551 C1 and DE 10 2004 063 599 A1.

In this step, the sol is, for example via a pressure vessel, blown out through a die plate with individual dies (pressure in the vessel 1-100 bar, preferably 20 to 30 bar).

The spinning chimney typically has a length of 1-5 m, advantageously 2 m. The climate in the spinning chimney is set in a controlled manner with regard to temperature and humidity. Preference is given to temperatures between 20° C. and 30° C. and dew point −5 to 10° C., and/or humidity of 20 to 40% relative humidity, preferably 20-25% relative humidity and more preferably about 20% relative humidity.

After falling through the spinning chimney, the fibres are dimensionally stable and are laid out on an oscillating table. The mesh size of the fibre structure thus formed is established, inter alia, via the oscillation rates. These are a few cm/s. By virtue of motion along two axes, a narrow-mesh fibre structure (web) is formed, in which, based on TEOS as the Si-containing starting compound, generally still more than 25 to 33% of the ethoxy groups are present.

Especially when the inventive materials are used for wound treatment, the basis weight of the fibre material is preferably at least 90 g/m2 and more preferably at least 150 g/m2. The thickness of the wound covering (consisting of the spun nonwoven) is preferably at least 0.8 mm and more preferably at least 1.5 mm. The fibre diameter is preferably at least 45 µm.

The silica gel fibre materials and products resulting from the process according to the invention, i.e. for example filaments, fibres, fibrous nonwoven webs and/or wovens, possess excellent biodegradability and bioabsorbability.

A further advantage of the present invention is that silica gel fibre materials produced according to the present invention, when compared with fibres obtained by the process of DE 196 09 551 C1, have distinctly improved values in cytotoxicity tests in tests in the presence of L929 mouse fibroblasts (see Example 1 and Comparative Example). Products produced from the silica sol material of the present invention are therefore notable for a particularly good biocompatibility. The present invention's filaments, fibres or fibrous nonwoven webs can therefore be used with advantage as biodegradable and/or bioabsorbable materials and products in human medicine or medical technology.

Irrespective of this, it has been shown experimentally that the inventive fibres and fibrous nonwoven webs have improved wound healing properties. More particularly, the materials of the present invention can therefore be used with advantage in the sector of wound treatment and wound healing. Filaments can be used for example as surgical suture or as reinforcing fibres. Fibre webs in accordance with the present invention can be used with particular advantage in the management of superficial wounds.

The present invention's biodegradable and bioabsorbable fibres and fibrous nonwoven webs are obtainable by a controlled hydrolysis condensation reaction of the above-mentioned silicon compounds and nitric acid acidified water by the following steps:

a) conducting a hydrolysis condensation reaction of one or more silicon compounds of the formula I $$SiX_4 \qquad (I)$$

where the X radicals are the same or different and denote hydroxyl, hydrogen, halogen, amino, alkoxy, acyloxy, alkylcarbonyl and/or alkoxycarbonyl and are derived from alkyl radicals which constitute optionally substituted straight-chain, branched or cyclic radicals having 1 to 20 carbon atoms, preferably having 1 to 10 carbon atoms, and may be interrupted by oxygen or sulphur atoms or by amino groups, under acidic catalysis at an initial pH of 0 to ≤7 in the presence or absence of a water-soluble solvent at a temperature of 0° C. to 80° C., preferably at 20-60° C., more preferably at 20 to 50° C., for example at room temperature (about 20° C. to about 25° C.) or about 37° C., for at least 16 h, preferably for at least 18 h, b) then evaporating to form a single-phase solution having a viscosity ranging from 0.5 to 2 Pa·s at a shear rate of 10 s$^{-1}$ at 4° C., c) then cooling this solution, and d) subjecting the cold solution to a kinetically controlled ripening to form a homogeneous sol, and e) extruding the sol obtained in d) in a spinning operation.

When TEOS, for example, is used as silicon compound in the hydrolysis condensation reaction of step a), a homogeneous solution is obtainable after the evaporation in step b), given sufficient hydrolysis time. A kinetically controlled reaction can take place in step c) during the ripening time at low temperature. The mixture can then be present in step d) in the dissolved state, as a homogeneous single-phase dope, and thus be recovered as spinnable sol dope.

The fibres or fibrous nonwoven webs produced in accordance with the present invention may in this respect be used advantageously as bioabsorbable and/or bioactive materials in human medicine, medical technology, filter technology, biotechnology or the insulating materials industry. In particular, the materials produced in accordance with the present invention may be used advantageously in the field of wound treatment and wound healing. Fibres may, for example, be used as surgical suture or as reinforcing fibres. Fibrous webs can be used particularly advantageously in the treatment of surface wounds, in the filtration of body fluids (e.g. blood) or in the bioreactor sector as a cultivation aid.

A further embodiment of the invention may be a drug delivery system and/or a medicament formulation, a micropowder and/or a nanopowder.

Such powder forms may be obtained, for example, by admixing the inventive silica sol with a desired active ingredient, for example one or more medicaments (as a result of a further hydrolysis condensation reaction, the active ingredient may optionally also be bound covalently), and a homogeneous mixture is obtained. Especially in the case of addition of thermally sensitive active ingredients, the mixture of sol and active ingredient(s) is subjected to a gentle drying step, for example a spray-drying or freeze-drying step. When the active ingredient is not thermally sensitive or one is not added at all, the drying can also be brought about at (significantly) elevated temperatures. This preferably forms a bioabsorbable and/or bioactive silica gel matrix around the active ingredient. This matrix is especially also suitable for the encapsulation of liquid active ingredients. Liquids can be enclosed in the matrix with long-term stability and be released again in a controlled manner. The encapsulation enables the mechanical and chemical stabilization of the active ingredients, the improved handling of such liquid active ingredients and medicaments, and helps to prevent uncontrolled volatilization of the active ingredients. It is of course also possible for further substances and/or assistants appropriate for the particular use to be present in the final formulation (powder). The particles of an inventive micropowder preferably have a size (a mean diameter) of 0.01 µm to 100 µm, especially 0.1 µm to 20 µm. The nanopowder particles generally have a size (a mean diameter) of 100 nm.

In a further embodiment, a mixture of at least one active ingredient can be poured into a mould with the inventive silica sol. After the drying, a monolith can be obtained in this way. Such monoliths may be used, for example, subcutaneously as a drug delivery system in the form of massive implants. They may be used, for example, as a depot for contraceptives and release the active ingredient over a prolonged period. Such inventive implants have a good biocompatibility. The monoliths may preferably have a diameter of ≥0.5 mm. Alternatively, the monoliths may also be comminuted and ground to powder.

In a further embodiment, the silica sol can be coated by customary coating processes, for example by immersing the body to be coated into the silica sol, by casting or by spin-coating or spraying the silica sol. Preference is given to coating the silica sol onto coated tablets or capsules. To this end, pressed pulverulent medicament mixtures are provided with a bioabsorbable and/or bioactive coating consisting of the inventive silica sol. This allows the release of (further)

active ingredients (for example via the layer thickness and/or the layer sequence) within the formulation to be controlled. Such a coating can, however, also be applied to body part implants, which improves the (biological) compatibility of the implants, for example alleviates or prevents rejection reactions.

In a further embodiment of the invention, highly viscous sols, especially hydrogels, can be supplemented or replaced by the inventive silica gel. The highly viscous sols and the hydrogels are used in medicine and in cosmetics as an active ingredient or medicament carrier. Generally, hydrogels are used in many cases in the treatment of large-area wounds (wound treatment and wound healing). Advantageously, the addition of the silica sol allows the biocompatibility and hence the wound healing to be improved. In this respect, the inventive hydrogels can be used as bioabsorbable and/or bioactive products in medicine, especially human medicine or medical technology.

The present invention further relates to a process for in vitro propagation of cells, wherein a fibre matrix composed of an inventive fibre serves as a cell support substance and/or guide structure for the extracellular matrix formed by the cells, or gives the cells the possibility of finding a three-dimensional arrangement which allows the cells to propagate and/or to achieve their genetically determined differentiation. The advantages of the process according to the invention arise, by way of example, from Example 3.

The cells used may, for example, be undifferentiated pluripotent stem cells or genetically modified or native differentiated cells of different types and degrees of differentiation.

The cells to be applied to the fibre matrix adhere to the matrix or are propagated principally in a two-dimensional manner on this matrix in order together to form an extracellular matrix or messenger substances (hormones). The fibre matrix preferably forms an areal element, especially in the form of a nonwoven or woven fabric of inventive fibres. This fibre matrix is preferably porous, such that the cells introduced/applied penetrate it, assume a three-dimensional distribution and, according to their genetically determined differentiation or a differentiation induced by added differentiation factors, can induce three-dimensional tissue and organ growth or release messenger substances. In an alternative embodiment of the invention, the matrix, as an impervious fibre mesh impenetrable by the cells introduced/applied, is formed with the means of two-dimensional cell distribution and of the simultaneous possibility of three-dimensional tissue and organ growth in the sense of a composite graft.

The inventive in vitro propagation process preferably serves for the in vitro production of cell composites, tissues and/or organs.

The invention relates preferably to a cell composite, tissue and/or organs producible by the process described above. Such a cell composite, such a tissue and/or such organs is/are suitable, for example, as an in vitro model for medicament-tissue-organ interactions. To produce tissues outside the human body, various processes are employed, which are combined under the generic term "tissue engineering". For this purpose, according to the tissue type, cells are isolated from their existing tissue composite and propagated. Thereafter, the cells are either applied to flat materials of different consistency or introduced into porous or gel materials, and the tissue ripening is induced thereby and optionally stimulated by differentiation factors. The tissue ripening can be effected outside or inside the body. The inventive fibre matrix has the advantage that it is biodegradable and/or bioabsorbable, but—as Example 3 shows—in spite of the in vitro propagation, retains its 2- or 3-dimensional form over a certain period. The invention accordingly preferably relates to a cell composite, tissue and/or organs comprising a fibre matrix of polysilicic acid, preferably produced from the inventive fibres, wherein the biodegradable and/or bioabsorbable fibre matrix, after a period of time of 4 weeks after the first in vitro cell colonization, is at least 60%, preferably at least 70% and more preferably at least 80% identical to the original 2- or 3-dimensional form of the fibre matrix. For example, the inventive fibre matrix degrades and/or absorbs in such an embodiment preferably only after application/introduction of the cell composite, tissue and/or organ onto/into an animal or human body.

According to the cell type, the cells must either be released beforehand from their matrix composite by enzymatic digestion or by mechanical separation, or induced to grow by application or introduction onto/into a nutrient medium under physiological conditions. In this case, the abovementioned fibre matrix functions as a guide structure for the cell growth or as a guide structure for the accumulation of extracellular matrix and tissue constituents. According to the invention, the fibre material can be employed in various arrangements. Which arrangement should be selected is known to the person skilled in the art depending on the (cell) tissue to be produced. The possible arrangements are as follows:

1) as an areal element, i.e. as an impervious fibre mesh which enables penetration over and above the dimension of the cells applied, albeit only limited (i.e. the average size of the holes/fibre or mesh interstices is in no way greater, but preferably smaller than the average size of the cells to be cultivated; thus, the cells can "grow into the fibres", but only in such a way that they adhere well on the substrate of the fibres), with essentially the only possibility, but at least primary possibility, of two-dimensional cell distribution and a flat cell, tissue and organ growth;

2) as a three-dimensional element, i.e. as a porous fibre mesh penetrable by the cells (i.e. the average size of the holes/fibre or mesh interstices is in no way smaller, but preferably greater than the average size of the cells to be cultivated), with the possibility of three-dimensional cell distribution and spatial cell, tissue and organ growth; 3) as a combination of 1) and 2) in the sense of a "composite graft" or organ by combination of cells, tissues or organs and surface covering tissue (e.g. organ capsule)

3) this variant is possible for tissue structures which are composed of several cell types. For example, vessels consist of endothelium and connective tissue, the endothelium with a flat structure serving to line a blood vessel, while the connective tissue functions as the support substance of the vessel and forms the three-dimensional hollow structure. The combination of 1) as the areal element for the growth of endothelium and 2) as a three-dimensional element for the growth of connective tissue ultimately allows a vessel to be reconstructed.

Some tissue or cell types which are particularly suitable for propagation/production by means of one of the three variants and are accordingly preferred in accordance with the invention are listed below.

For application 1), preferably the following tissues: epithelium, endothelium, urothelium, mucosa, dura, connective tissue; and preferably the following cells: pluripotent stem cells, chondrocytes (cartilage; for chondrocyte propagation, a two-dimensional medium is needed; for chondrocyte differentiation and cartilage matrix formation, in contrast, a three-dimensional medium is needed. Here, with regard to cartilage, what is meant is only the cells when they dedifferentiate and propagate. The differentiation follows in application 2), osteocytes (bone; either two- or three-dimensional, the same applies here as for the chondrocytes), nerve cells (nerves), hair cells (inner ear hearing organ) or their precursor cells of any stage of differentiation (e.g. pluripotent stem cells).

For application 2), the following cells: the cells described for application 1) after their two-dimensional propagation, organ-specific cells (e.g. hepatocytes, nephrocytes, cardiomyocytes, pancreocytes), cells of the CNS with/without endocrine function, e.g. retina, neurocytes, pineal gland, dopaminergic cells, vessel-forming cells (e.g. angiocytes), cells with endo- or exocrine function (e.g. islet cells, adrenal gland cells, salivary gland cells, epithelial bodies, thyrocytes), cells of the immune system (e.g. macrophages, B cells, T cells or their precursor cells of any differentiation stage, such as pluripotent stem cells). The cells of the immune system are bred in three dimensions because, in the tissue, after penetrating the blood-tissue barrier, they meet a three-dimensional structure according to the tissue type and display their action there in three dimensions.

For application 3), the following cells/tissue/organs: trachea, bronchia, vessels, lymph tissue, urethra, ureter, kidney, bladder, adrenal gland, liver, spleen, heart, vessels, thyroid gland, tonsils, salivary glands, brain, muscles (smooth, skeletal), intervertebral discs, meniscus, heart, lung, gall bladder, oesophagus, intestine, eye.

Examples 1 to 3 of EP 1 262 542 describe, by way of example, possible applications with fibres which are known from DE 196 09 551 C1. A further possible use of the material employed in the invention is the colonization of the material with cells which have an endo- or exocrine function and release active ingredients (e.g. hormones, interleukins, inflammation mediators, enzymes) which display an effect in the organism or outside it. This means that the material used in accordance with the invention, when colonized with cells having endo- or exocrine function, can also serve to produce the abovementioned active ingredients outside the body, which are then made available to the body as medicaments by means of known methods. An action displayed outside the body can serve to influence tissue or cells with the substance released.

A further use of the matrix is as a bioabsorbable bioimplant as a guide splint for endogenous wound healing under or at the level of the skin, mucous membrane or within the body in the course of operations on organs and tissues. To this end, the material is, if possible, introduced into the wound or organs/tissues, for example during an operation, if possible by a doctor as an areal element or three-dimensional element, directly or together with the substances or medicaments which promote wound healing. The properties of the bioabsorbable inorganic material used in accordance with the invention in the form of fibres cause only a slight change to the tissue medium for the cells to be grown; more particularly, no acidic medium arises, with the consequence that an adverse influence on tissue and organ differentiation is prevented. In addition, irrespective of the pH of the tissue, there is complete degradation of the material. As a result of the simultaneous tissue or organ formation, the vital tissue is constantly available with the possibility of penetration by antiinfectious medicaments in the event of unwanted colonization with pathogens (infection). In addition, the fibre matrix can be admixed with active ingredients of different substance groups, with the possibility of a positive influence on tissue and organ differentiation by development of an active and passive action at the site of use, but also by development of action at a removed site of action. These include especially, firstly, anti-infectious active ingredients, but secondly also active ingredients which promote and modulate wound healing, the inflammation reaction and tissue differentiation, for example firstly growth factors (IGF, TGF, FGF, etc.) and secondly glucocorticoids and interleukins, but also chemotherapeutic drugs and immunosuppressants.

The bioabsorbable inorganic fibres used in accordance with the invention enable adherence of the cells employed with the possibility of propagation of the cells along the fibres, but also with the possibility of formation of a tissue or organ matrix. Simultaneously with the propagation of the cells or the formation of a tissue or organ matrix, the fibre structure is degraded. Ideally, the tissue structure, organ structure or cell structure is correlated with the degradation rate of the fibre material by variation of the condensation of the fibres. The lesser the progress of the condensation process (i.e. the elimination of water and hence the polycondensation), the better the material can be degraded. The highest OH content and hence the most rapidly degradable fibres are obtained in the case of freshly spun fibres, which are subsequently placed into ethanol. The condensation process is also influenced by the spinning parameters, i.e. drawing rate, atmosphere, spinning temperature, etc. Fibres thus produced are biodegradable and bioabsorbable and are dissolved in weakly basic, body-like fluids with degradation rates of 10 nm to 100 nm of fibre radius per day, the degradation rate being correlated to the number of silanol groups of the fibre. A further aspect of the present invention relates to the use of the inventive cells, organs and tissue after they have been admixed with medicaments and/or active ingredients as an in vitro model for medicament-tissue-organ interactions. As a result, animal experiments can be minimized or avoided.

The invention further more preferably relates to a process for producing a skin implant, wherein skin cells are applied to the surface of a nutrient solution and allowed to grow, and an areal element composed of an inventive fibre is placed onto the nutrient solution.

The invention further relates, in a preferred subject of the invention, to a skin implant consisting of skin cells and an areal element comprising inventive fibres. An areal element (preferably planar) enables flat and hence rapid growth of skin cells, optionally with use of infiltrated medicaments.

The invention will now be more particularly described with reference to examples without being restricted thereto.

All reported viscosities were measured with viscometers from Physika (MCR 300 and MCR301) at a shear rate of 10 $s^{-1}$ at 4° C.

INVENTIVE EXAMPLE 1

Silica sol and bioabsorbable and biodegradable silica gel material

By way of reactants for the hydrolysis condensation, 4 mol of TEOS (tetraethoxysiloxane) were introduced as initial charge, in ethanol, into a reaction vessel and 7 mol of water were added in the form of 0.01 N $HNO_3$ solution and were mixed with one another by stirring. The mixture was stirred at room temperature for 8 days. The solution from the hydrolysis condensation reaction was subsequently converted into an almost water- and ethanol-free solution by evaporating and condensing in a glass beaker at 70° C. This solution was single phase, contained no solids and had a viscosity of 1 Pa·s (shear rate of 10 s$^{-1}$ at 4° C.). The solution was cooled to 4° C. and subjected to ripening at this temperature. Following a ripening time of 18 days, a homogeneous single-phase sol dope having a viscosity of 43 Pa·s (shear rate 10 s$^{-1}$ at 4° C.) was obtained. The sol dope had no discernible solid phase. The homogeneous sol dope was spinnable into fibres. It is also referred to as spinning dope.

The fibres were produced in a conventional spinning system. To this end, the spinning dope was filled into a cooled pressure cylinder at −15° C., which was pressurized with an air pressure of 20 bar. The resulting force forced the sol through dies to form filaments. The filaments had a diameter of 5 and 100 nm, depending on die diameter.

The free-flowing, honey-like filaments fell under their own weight into a spin shaft under the pressure cylinder, where they reacted to form a substantially solid form and to form dimensionally stable filaments. The filaments were still reactive at their surface, so that they were able to stick to one another along their areas of contact when landing on an optionally provided traversing table. Adjustable stroke cycles on the part of the traversing table created further cross-links between the fibres to form a fibrous nonwoven web.

Advantageously, the filaments obtained according to the present invention are drier than fibres obtained under comparable spinning conditions in the process of DE 196 09 551 C1. As a result, in the subsequent fabrication of webs, less crosslinked and hence more flexible webs were obtained according to the present invention. The fibrous nonwoven web produced according to the present invention was subjected to a cytotoxicological test to ISO 10993-5 (1999); EN 30993-5 (1994).

Following extraction of the web material with DMEM (Dulbecco's modified Eagle Medium), the extract was sterile-filtered and admixed with FCS (foetal calf serum; 10% FCS in extract). This FCS-admixed extract was applied under sterile conditions to L929 mouse fibroplast cells and stored for 48 h at 37° C. and $CO_2$ partial pressure of 5%. Triton X 100 was used as toxic control substance and cell culture medium was used as non-toxic control substance.

To determine the cell count, the cells were fixed and stained with methylene blue. After acidic extraction of the methylene blue, the dye content was detected by means of photometry and the absorbance was compared with a standard curve in order to determine the cell count with reference to the dye absorbance. The measurement of the cell count compared to the control showed that the inventive silica gel material had no cytotoxic properties. Measurements of the protein content (after alkaline lysis and protein content determination by the Bradford method) and the release of lactate dehydrogenase (LDH; photometric method) confirmed the results.

COMPARATIVE EXAMPLE

Under the same conditions, toxicity measurements were carried out on a web material which was produced similarly to the example in DE 196 09 551 C1 using a hydrolysis condensation time of 1.5 h. In this case, only 50% of the total reaction batch could be spun. The resulting fibre material tested positive for cytotoxicity.

COMPARATIVE EXAMPLE 2

In a further study, five different inventive fibre webs (KG211, KG226, AEH06KGF553, AEH06KGF563 and AEHKGF565) were compared with an absorbable control wound therapeutic system (Promogran®) in a 3-month wound healing study on guinea pigs.

Differences between the inventive fibre webs are found through the different production parameters listed in Table 1 below.

TABLE 1

| | Parameter/description | KG211 | KG226 | AEH06KGF553 | AEH06KGF563 | AEHKGF565 |
|---|---|---|---|---|---|---|
| Hydrolysis/condensation | | | | | | |
| Apparatus | Type of reaction vessel | 2 l one-neck round-bottom flask | 2 l one-neck round-bottom flask | Stirred tank | Stirred tank | Stirred tank |
| | Mixing | Stirrer bar | Stirrer bar | Crossbar | Crossbar | Crossbar |
| Process | Termination criterion/aim of the process step | Reaction time 18 h | Reaction time 18 h | Reaction time 18 h | Reaction time 18 h | Reaction time 18 h |
| | Weighing + introduction of TEOS | 562.49 g | 562.49 g | 562.49 g | 562.49 g | 562.49 g |
| | Weighing + addition of ethanol | 156.8 g | 156.8 g | 156.8 g | 156.8 g | 156.8 g |
| | Mixing | 15 min | 15 min | 15 min | 15 min | 15 min |
| | Weighing + provision of water | 60.38 g | 60.38 g | 60.38 g | 60.38 g | 60.38 g |
| | Weighing + addition of 1N HNO3 | 27.81 g | 27.81 g | 27.81 g | 27.81 g | 27.81 g |
| | Mixing of 1N HNO3 + water | Tilting | Tilting | Tilting | Tilting | Tilting |
| | Heat treatment | Autothermal, i.e. conduct at RT after exothermic reaction | Autothermal, i.e. conduct at RT after exothermic reaction | First autothermal, from reaction time 3:00 h T = 25° C. | First autothermal, from reaction time 0:20 h T = 70° C. | First autothermal, from reaction time 0:20 h T = 50° C. |
| Reactive evaporation | | | | | | |
| Apparatus | Type of reaction vessel | Rotary evaporator | Rotary evaporator | Stirred tank | Stirred tank | Stirred tank |
| | Mixing | Rotary evaporator | Rotary evaporator | Crossbar | Crossbar | Crossbar |
| | Type of heat treatment | Water bath | Water bath | Jacket heating | Jacket heating | Jacket heating |

TABLE 1-continued

|  | Parameter/description | KG211 | KG226 | AEH06KGF553 | AEH06KGF563 | AEHKGF565 |
|---|---|---|---|---|---|---|
| Process | Medium for the entrainment stream | Vacuum | Vacuum | Control air | Control air | Control air |
|  | Supply of the entrainment stream | — | — | Glass frit | Glass frit | Glass frit |
|  | Removal of the ethanol-containing waste air | Rotary evaporator connection | Rotary evaporator connection | Opening in the lid | Opening in the lid | Opening in the lid |
|  | Termination criterion/aim of the process step | Mass loss 61.7% | Mass loss 61.7% | Dyn. viscosity (4° C., 10 s-1): 1 Pas | Dyn. viscosity (4° C., 10 s-1): 1 Pas | Dyn. viscosity (4° C., 10 s-1): 1 Pas |
|  | Mixing | 25 rpm | 25 rpm | 60 rpm | 45 rpm | 45 rpm |
|  | Heat treatment | 70° C. | 70° C. | 60° C. | 75° C. | 70° C. |
|  | Air stream | Vacuum down to approx. 400 mbar | Vacuum down to approx. 400 mbar | 3.8 m3/h | 3.0 m3/h | 3.0 m3/h |
|  | Reactive evaporation time |  |  | 05:40 | 05:30 | 06:30 |
|  | Filtration | Screen | Screen | Filter | Filter | Filter |
|  | Ripening |  |  |  |  |  |
| Apparatus | Ripening vessel | 500 ml PP cup | 500 ml PP cup | 500 ml PP cup | 500 ml PP cup | 500 ml PP cup |
|  | Storage during ripening | Refrigerator | Refrigerator | Refrigerator | Refrigerator | Refrigerator |
| Process | Termination criterion/aim of the process step | Dyn. viscosity 39.2, loss factor 3.12 | Dyn. viscosity 41.2, loss factor 2.69 | Dyn. viscosity 45, loss factor 2.6 | Dyn. viscosity 73, loss factor 4.7 | Dyn. viscosity 44, loss factor 3.6 |
|  | Ripening temperature | 4° C. | 4° C. | 4° C. | 4° C. | 4° C. |
|  | Type of storage of the ripening cup | At rest, upright | At rest, upright | At rest, upright | At rest, upright | At rest, upright |
|  | Ripening time | 28 d | 39 d | 11 d | 10 d | 19 d |
|  | (Intermediate) storage |  |  |  |  |  |
| Apparatus | Storage vessel | 500 ml PP cup | 500 ml PP cup | 500 ml PP cup | 500 ml PP cup | 500 ml PP cup |
|  | Location of storage | Freezer | Freezer | Freezer | Freezer | Freezer |
|  | Storage temperature | −80° C. | −80° C. | −80° C. | −80° C. | −80° C. |
|  | Type of storage of the ripening cup | At rest, upright | At rest, upright | At rest, upright | At rest, upright | At rest, upright |
|  | Spinning |  |  |  |  |  |
|  | Die plate | 7 dies, D = 150 μm | 7 dies, D = 150 μm | 7 dies, D = 150 μm | 7 dies, D = 150 μm | 7 dies, D = 150 μm |
|  | Spinning tower | approx. 2 m | approx. 2 m | approx. 2 m | approx. 2 m | approx. 2 m |
|  | Oscillating table | Single-axis | Single-axis | Double-axis | Double-axis | Double-axis |
|  | Thawing of a frozen sample in a refrigerator | 01:30.00 h | 01:45.00 h | 01:40.00 h | 01:30.00 h | 02.00.00 h |
|  | Heat treatment of the spinning vessel |  |  |  |  |  |
|  | Wait time after filling of the spinning vessel | 03:30.00 h | 03:00.00 h | 03:30.00 h | 02:10.00 h | 03:00.00 h |
|  | Pressure in the spinning vessel | 20 bar | 20 bar | 30 bar | 20 bar | 20 bar |
|  | Temperature in the spinning tower | 21° C. | 22° C. | 23° C. | 23° C. | 22° C. |
|  | Humidity in the spinning tower | 20% rh | 33% rh | 34% rh | 20% rh | 22% rh |
|  | Spinning time for 1 nonwoven | 6 min | 5 min | 6 min | 12 min | 6 min |
|  | Movement pattern of oscillating table | Stroke length: 28 cm Stroke cycles: 16/min | Stroke length: 28 cm Stroke cycles: 16/min | Stroke length: 28 cm Stroke cycles: 16/min | Stroke length: 28 cm Stroke cycles: 16/min | Stroke length: 28 cm Stroke cycles: 16/min |
|  | Cut piece |  |  |  |  |  |
| Apparatus | Cut piece | 5 × 5 cm | 5 × 5 cm | 5 × 5 cm | 5 × 5 cm | 5 × 5 cm |
|  | Product analysis |  |  |  |  |  |
|  | Basis weight | 185 g/m2 | 165 g/m2 | approx. 200 g/m2 | 90 g/m2 | 15 g/m2 |
|  | Thickness of the wound covering | 1.8 mm | 2.1 mm | 1.3 mm | 0.8 mm | 1.4 mm |
|  | Fibre diameter | 44 μm | 56 μm | 61 μm | 45 μm | 50 μm |

TABLE 1-continued

| Parameter/description | KG211 | KG226 | AEH06KGF553 | AEH06KGF563 | AEHKGF565 |
|---|---|---|---|---|---|
| Behaviour in the bending test | Very flexible, easy splitting into individual layers | Very flexible, easy splitting into individual layers | Partial fracture, fracture of the outermost layers | No intrinsic stability, extremely soft and flexible | Very flexible, no fracture, soft, some splitting into individual layers |
| Content of free ethanol | 0.61 w % | 0.79 w % | 0.87 w % | 0.31 w % | 0.67 w % |
| Ethoxy group content | 31.3 w % | 32.1 w % | 27 w % | 32.8 w % | 33.2 w % |

For the study, dermo-epidermal wounds were established by surgery in 36 guinea pigs. In each animal, dermis and epidermis were removed on both sides of the spinal column in an approximate area of 6.25 cm2 (2.5×2.5 cm). The wounds were generated by a scalpel. The panniculus carnosus was not injured. The inventive wound coverings and Promogran® were placed into the particular wounds. The materials were covered with a non-adhesive wound dressing (URGOTUL®) and a semi-permeable adhesive polyurethane film (TEGADERM® or OPSITE®). A cohesive bandage (gauze and Elastoplast®) protected the wound dressings over the wound. Each fibre web or the control material was tested on 5 animals, corresponding to 10 wounds (n=10). At different time intervals, the wound healing was evaluated by macroscopic, morphometric and histological tests.

In all wound coverings tested, no local intolerance was observed. Morphometric tests showed that those wounds which had been treated with Promogran® achieved 50% wound closure somewhat earlier than those treated with the webs. In order to achieve complete (100%) or virtually complete (75%, 95%) wound closure, the time for Promogran® was, however, somewhat slower compared to most webs. 100% healing was achieved after an average of approx. 23 days for KG211 and KG226, after an average of approx. 24 days for AEH06KGF553, AEH06KGF563 and AEH06KGF565, and only after an average of 26 days for Promogran®.

Histological tests of KG211 animals 28 days after the generation of the wound showed very good wound healing (see FIG. 1a). Only the local tissue reaction was not yet entirely stabilized, since isolated macrophages were still observed. Irrespective of this, the granulation tissue was inconspicuous, exhibited normal thickness and was covered by a newly formed continuous epithelial layer.

Figure 1B:
FIG. 1b depicts results of histological tests on the Promogran® animals 28 days after generation of wounds.

Histological tests on the Promogran® animals 28 days after generation of the wound showed a highly vacuolized granulation tissue permeated by polymorphonuclear cells (see FIG. 1b). In contrast to KG211, the granulation tissue was not covered by an epithelial layer.

The inventive wound coverings accordingly exhibit shortened wound healing with simultaneous generation of a better granulation layer and minimization of inflammation processes compared to Promogran® in the first 4 weeks of wound healing.

INVENTIVE EXAMPLE 3

The inventive fibre matrix KG119 composed of biodegradable and/or bioabsorbable fibres as the cell support substance, and also collagen and polyglycolic acid (PGA), were sterilized with gamma rays and placed into a full medium for one hour in an incubator. The fibre matrix KG119 relates to a web as the areal element. It was produced according to the process parameters shown in Table 2. The cut pieces were punched out in the shape of circles (see FIG. 3):

TABLE 2

| Parameter/description | | KG119 |
|---|---|---|
| Hydrolysis/condensation | | |
| Apparatus | Type of reaction vessel | 2 l one-neck round-bottom flask |
| | Mixing | Stirrer bar |
| Process | Shutdown criterion/aim of the process step | Reaction time 18 h |
| | Weighing + introduction of TEOS | 562.49 g |
| | Weighing + addition of ethanol | 156.8 g |
| | Mixing | 15 min |
| | Weighing + provision of water | 60.38 g |
| | Weighing + addition of 1N HNO3 | 27.81 g |
| | Mixing of 1N HNO3 + water | Tilting |
| | Heat treatment | Autothermal |
| Reactive evaporation | | |
| Apparatus | Type of reaction vessel | Open PP cup |
| | Mixing | None |
| | Type of heat treatment | Water bath |
| | Medium for the entrainment stream | Compressed air |
| | Supply of the entrainment stream | Transverse flow through cup |
| | Removal of the ethanol-containing waste air | Uncontrolled to environment |
| Process | Shutdown criterion/aim of the process step | Mass loss 61.7% |
| | Mixing | 0 |
| | Heat treatment | 70° C. |
| | Air stream | Uncontrolled to environment |
| | Reactive evaporation time | Mass loss |
| | Filtration | Screen |
| Ripening | | |
| Apparatus | Ripening vessel | 500 ml PP cup |
| | Storage during ripening | Refrigerator |
| | Determination of the progress of ripening | |
| | In-process control | Screen |
| Process | Shutdown criterion/aim of the process step | Dyn. Viscosity, 30 Pas before spinning, loss factor 3.22 |
| | Ripening temperature | 4° C. |
| | Type of storage of the ripening cup | At rest, upright |
| (Intermediate) storage | | |
| Apparatus | Storage vessel | 500 ml PP cup |
| | Location of storage | Freezer |
| | Storage temperature | −80° C. |
| | Type of storage of the ripening cup | At rest, upright |

TABLE 2-continued

| Parameter/description | | KG119 |
|---|---|---|
| Spinning | | |
| | Die plate | 7 dies, D = 150 μm |
| | Device for spooling the | after 1 h |
| | Spinning tower | approx. 2 m |
| | Oscillating table | Single-axis |
| | Temperature in the spinning tower | RT |
| | Humidity in the spinning tower | Approx. 30% rh |
| | Spinning time for 1 web | 6 min |
| | Movement pattern of oscillating table | Stroke length: 28 cm Stroke cycles: |
| | Conditioning of the web | 6 min |
| Cut piece | | 2.5 × 2.5 cm |

Before the cell colonization, the medium was renewed. Thereafter, human dermal fibroblast cells were added. The cells were cultured in 24-hole Falcon 351147 plastic plates.

The medium was changed every day. The cell colonization medium was Gibco Dulbecco's Modified Eagle's Medium 42430-250 supplemented with 10% foetal calf serum (FCS) and 100 units/ml of penicillin, 0.25 ng/ml of amphotericin B and 0.1 mg/ml of streptomycin as antibiotics. During the growth of the cells, after the initial change of medium, 50 μg/ml of ascorbic acid were added to the medium. Moreover, given the rising number of cells, it became necessary to admix the medium with a sodium bicarbonate solution buffer (7.5%, Sigma). The cell standards (control cells without cell support substance) were cultivated in customary tissue culture dishes and glass-based Iwaki plates.

The Alamar Blue assay was carried out with reagents from Serotec. These were diluted to 10% with HBSS (phenol-free) buffer, adjusted to 37° C. and sterile-filtered. The cell support substances comprising the cells were washed in PBS and then removed from their original plates and placed into tissue culture dishes and glass-based Iwaki plates.

Figure 2:
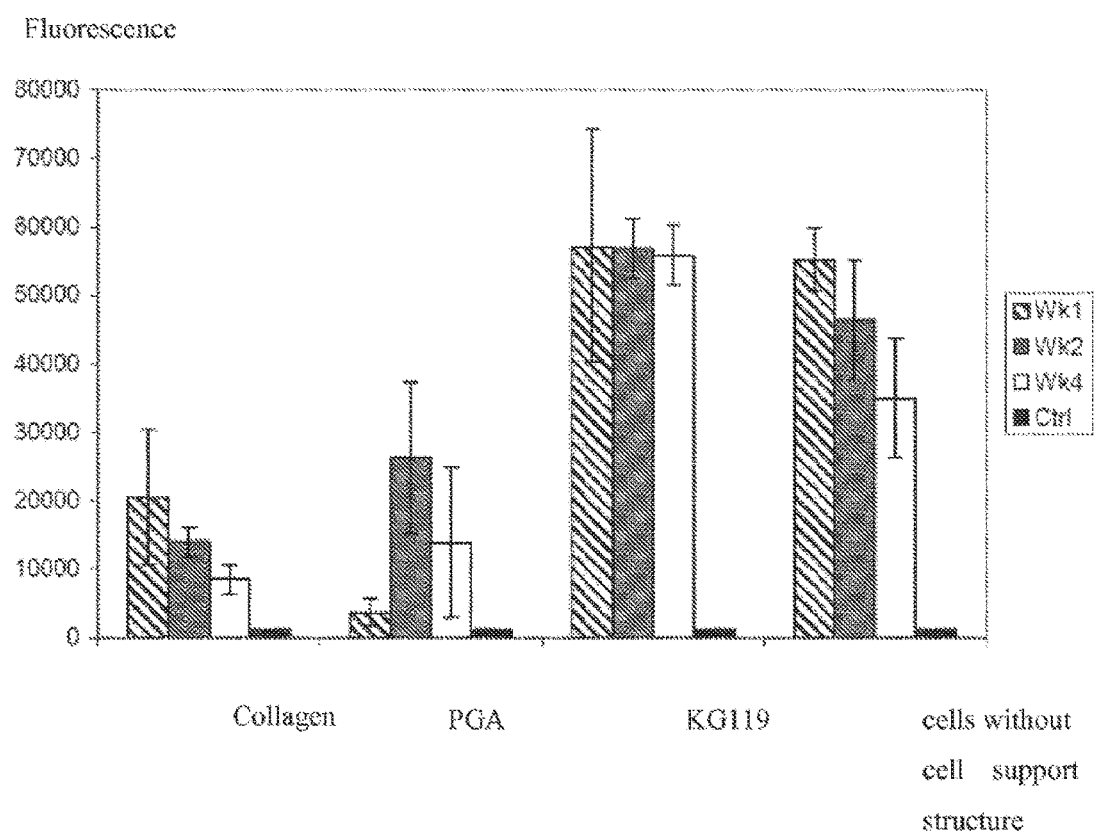
FIG. 2 depicts the comparative activity of the dermal fibroblasts on the different matrices of collagen, PGA and of the inventive fibre matrix KG119, and also cells without a support structure (control culture, "Ctrl") at cultivation times of one week ("Wk1"), two weeks ("Wk2"), and four weeks ("Wk4").

The metabolic activity measured with the Alamar Blue assay is a function of the cell count and the metabolic activity of the individual cells. FIG. 2 compares the activity (shown in the form of a fluorescence measurement) of the dermal fibroblasts on the different matrices of collagen, PGA and of the inventive fibre matrix KG119, and also cells without a support structure (control culture, Ctrl) at a cultivation time of one week (Wk 1), 2 weeks (Wk 2) and 4 weeks (Wk 4).

The primary adhesion of the cells to KG119 is strong and comparable to that of collagen. KG119 and collagen exceed PGA with regard to cell adhesion (data not shown). The longer the cells grow on the matrices, the more clearly the superiority of the KG119 fibre matrix is shown. FIG. 2 shows that KG119 exceeds the other cell support structures with regard to metabolic activity of the cells. The high metabolic activity is maintained over the entire measurement period (4 weeks). In contrast, collagen, PGA and cells without cell support structures cannot maintain the metabolic activity over this period. Only KG119 exhibits a high cell adhesion, cell proliferation with retention of the metabolic activity over the entire period.

Figure 3:
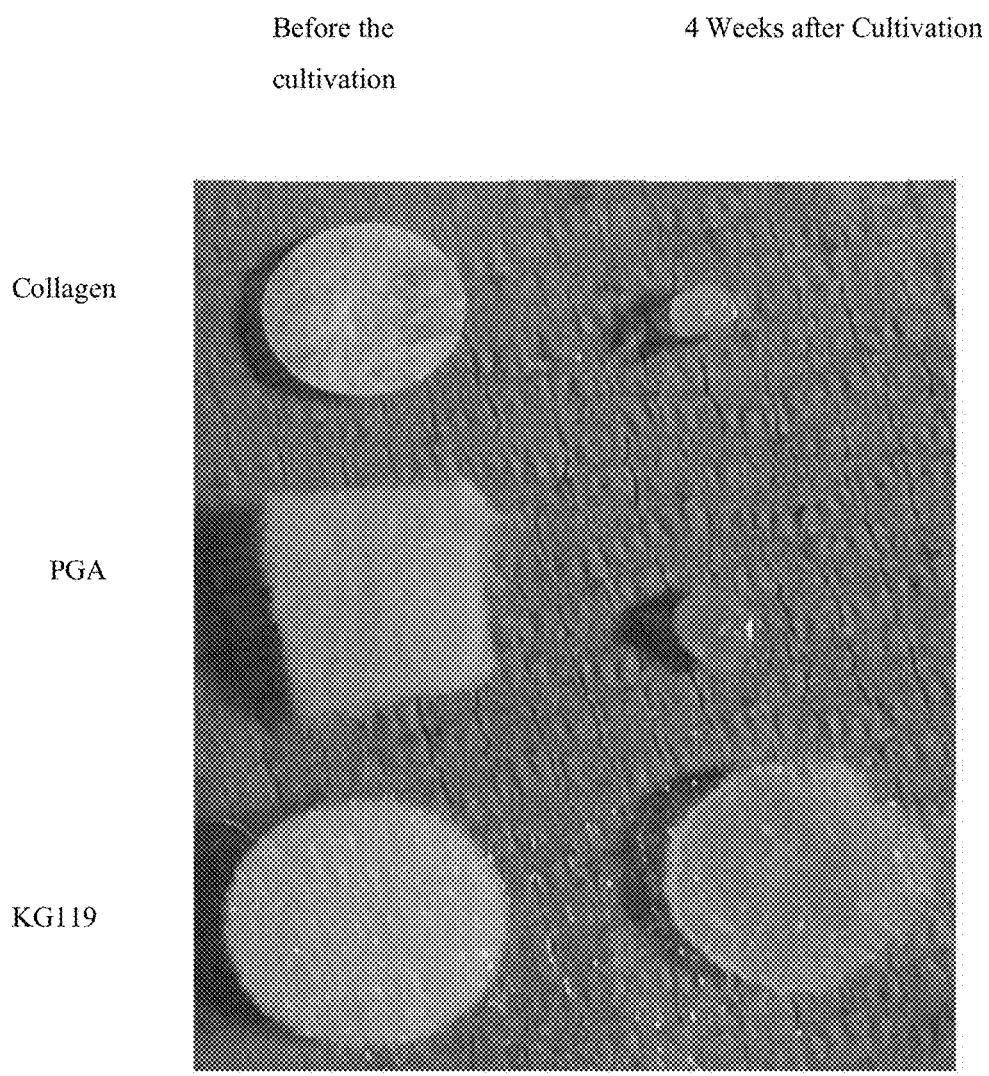
FIG. 3 depicts the cell support structures collagen, PGA and KG119 before cultivation with human dermal fibroblast cells and after four weeks of culture time.

FIG. 3 shows the cell support structures collagen, PGA and KG119 before the cultivation with human dermal fibroblast cells and after 4 weeks of culture time. Collagen and PGA cell support structures contract and degrade to a tight tissue ball. Only KG119 retains its original form. Within KG119, a tight dermal tissue mass has formed, and the fibres are connected firmly to the tissue.

The invention claimed is:

1. A silica fibers material produced by spinning a silica sol material obtained by
    a) conducting a hydrolysis condensation reaction of one silicon compound of formula (I)

$$SiX_4 \qquad (I)$$

where the X radicals denote ethoxy groups,
    under acidic catalysis at an initial pH of 0 to ≤7, in the presence or absence of a water-soluble solvent at a temperature of 0° C. to 80° C. for 24 h to 18 days,
    b) then evaporating to form a single-phase solution having a viscosity ranging from 0.5 to 2 Pa·s at a shear rate of 10 s$^{-1}$ at 4° C.,
    c) then cooling this solution, and
    d) subjecting the cold solution to a ripening to form a homogeneous sol, and
        wherein 27% to 33.2% of the ethoxy groups from the tetraethoxysilane are present in the silica fibers material.

2. The silica fibers material according to claim 1, wherein, for the acidic catalysis, the silicon compound and nitric acid acidified H$_2$O are used in a molar ratio in the range of 1:1.7 to 1:1.9, and the hydrolysis condensation reaction is conducted between 20 and 60° C.

3. The silica fibers material according to claim 1, wherein the hydrolysis condensation reaction in step a) is conducted at 20 to 60° C.

4. The silica fibers material according to claim 1, wherein step b) proceeds in a closed apparatus at a reaction temperature of about 30 to about 90° C.

5. The silica fibers material according to claim 1, wherein the solution in step c) is cooled down to 2° C. to 4° C.

6. The silica fibers material according to claim 1, wherein the ripening in step d) is effected at a temperature of 2° C. to 4° C.

7. The silica fibers material according to claim 1, wherein the ripening in step d) is carried on to a sol viscosity of 30 to 100 Pa·s at a shear rate of 10 s$^{-1}$ at 4° C. and a loss factor of 2 to 5 (at 4° C., 10 l/s, 1% deformation).

8. The silica fibers material according to claim 1, which comprises fibres, continuous filaments, fibrous nonwoven webs and/or wovens.

9. The silica fibers material according to claim 1, wherein the conducting of the hydrolysis condensation reaction is for 3 to 8 days.

10. The silica fibers material according to claim 1, wherein the conducting of the hydrolysis condensation reaction is with mixing at 20 rpm to 80 rpm.

11. The silica fibers material according to claim 1, wherein the conducting of the hydrolysis condensation reaction is for 3 to 18 days.

12. A process for producing a silica fibers material by spinning a silica sol material, which is extrudable to an extent of at least 70% of the overall reaction mixture, by
    a) conducting an 24 h to 18-day hydrolysis condensation reaction of one Si compounds of the formula (I)

$$SiX_4 \qquad (I)$$

in which the X radicals denote ethoxy groups,
    under acidic catalysis at an initial pH of 0 to ≤7, in the presence or absence of a water-soluble solvent at a temperature of 0° C. to 80° C., b) evaporating to form a single-phase solution having a viscosity ranging from 0.5 to 2 Pa·s at shear rate of 10 s⁻¹ at 4° C., c) cooling single-phase solution and d) ripening the cold solution to form a homogenous silica sol material, and wherein 27% to 33.2% of the ethoxy groups from the tetraethoxysilane are present in the silica fibers material.

13. A method of producing a silica fibers material by spinning a silica sol material comprising:

a) conducting a hydrolysis condensation reaction of one silicon compounds of formula (I)

$$SiX_4 \qquad (I)$$

where the X radicals denote ethoxy groups, under acidic catalysis at an initial pH of 0 to ≤7, in the presence or absence of a water-soluble solvent at a temperature of 0° C. to 80° C. for 24 h to 18 days, b) evaporating to form a single-phase solution having a viscosity ranging from 0.5 to 2 Pa·s at a shear rate of 10 s⁻¹ at 4° C., c) cooling this solution, and d) subjecting the cold solution to a ripening to form a homogeneous sol, and wherein 27% to 33.2% of the ethoxy groups from the tetraethoxysilane are present in the silica fibers material.

* * * * *